United States Patent
Le Maoult et al.

(10) Patent No.: US 9,359,424 B2
(45) Date of Patent: Jun. 7, 2016

(54) MULTIMERIC POLYPEPTIDES OF HLA-G INCLUDING ALPHA1-ALPHA3 MONOMERS AND PHARMACEUTICAL USES THEREOF

(75) Inventors: Joel Le Maoult, Melun (FR); Edgardo Delfino Carosella, Paris (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 1146 days.

(21) Appl. No.: 13/380,659

(22) PCT Filed: Jun. 25, 2010

(86) PCT No.: PCT/IB2010/052920
§ 371 (c)(1),
(2), (4) Date: Mar. 6, 2012

(87) PCT Pub. No.: WO2010/150235
PCT Pub. Date: Dec. 29, 2010

(65) Prior Publication Data
US 2012/0164164 A1 Jun. 28, 2012

(30) Foreign Application Priority Data
Jun. 25, 2009 (WO) .................. PCT/IB2009/006491

(51) Int. Cl.
*A61K 39/00* (2006.01)
*C07K 14/74* (2006.01)

(52) U.S. Cl.
CPC ......... *C07K 14/70539* (2013.01); *A61K 39/001* (2013.01)

(58) Field of Classification Search
None
See application file for complete search history.

(56) References Cited

U.S. PATENT DOCUMENTS

| 5,856,442 A | 1/1999 | Carosella et al. |
| 2004/0044182 A1* | 3/2004 | Hunt et al. .................. 530/350 |
| 2011/0189238 A1 | 8/2011 | Rouas-Freiss et al. |

FOREIGN PATENT DOCUMENTS

| WO | 2007 091078 | 8/2007 |
| WO | 2010 052228 | 5/2010 |
| WO | WO 2010052228 A1 * | 5/2010 |

OTHER PUBLICATIONS

LeMaoult et al., FASEB J. Sep. 2013;27(9):3643-51. doi: 10.1096/fj.13-228247. Epub Jun. 10, 2013.*
Rouas-Freiss et al., J Immunol Res. 2014;2014:359748. doi: 10.1155/2014/359748. Epub Mar. 31, 2014.*
Naji et al., Leukemia. Aug. 2012;26(8):1889-92. doi: 10.1038/leu.2012.62. Epub Mar. 5, 2012.*
U.S. Appl. No. 13/379,525, filed Dec. 20, 2011, Le Maoult, et al.
Shiroishi, M., et al., "Efficient Leukocyte Ig-like Receptor Signaling and Crystal Structure of Disulfide-linked HLA-G Dimer," The Journal of Biological Chemistry, vol. 281, No. 15, pp. 10439-10447, (Apr. 14, 2006) XP003007724.
International Search Report Issued Sep. 28, 2010 in PCT/IB10/052920 Filed Jun. 25, 2010.

* cited by examiner

*Primary Examiner* — Michael Szperka
(74) *Attorney, Agent, or Firm* — Oblon, McClelland, Maier & Neustadt, L.L.P.

(57) ABSTRACT

Multimeric polypeptides and pharmaceutical uses thereof; multimers comprising alpha3 and alpha1 peptides of an HLA-G antigen and methods of producing such multimers, pharmaceutical compositions comprising the same, as well as their uses for treating various diseases including organ/tissue rejection. Said multimers comprise at least two monomers, each of said monomers being selected in the group consisting of a peptide P2 of formula P1-X3 or X2-X3, wherein P1 is of formula X1-X2, wherein X1 represents a peptidic linker including a cysteine amino acid and X2 represents an alpha1 domain (or alpha1 peptide) of HLA-G and X3 represents an alpha3 domain of HLA-G.

19 Claims, 10 Drawing Sheets

(alpha3_L1) Peptide

Figure 1:
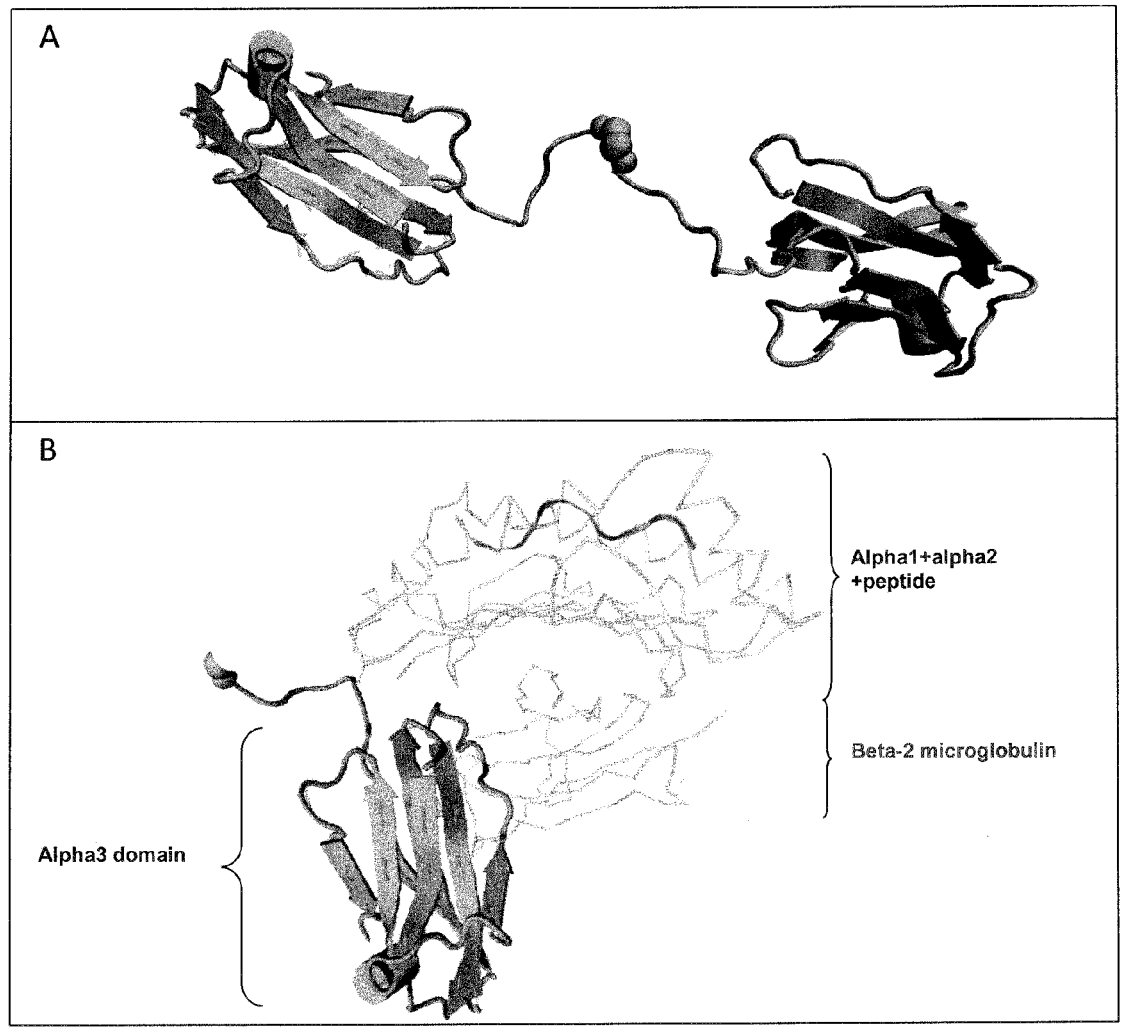

GCGGGGSGGGGSRADPPKTHVTHHPVFDYEATLRCWALGFYPAEIILTWQ
RDGEDQTQDVELVETRPAGDTFQKWAAVVVPSGEEQRYTCHVQHEGLP
EPLMLRWKQ (SEQ ID NO:3)

(alpha3_L2) Peptide

CASDSDFRVFQTDKEMLQRADPPKTHVTHHPVFDYEATLRCWALGFYPAEII
LTWQRDGEDQTQDVELVETRPAGDTFQKWAAVVVPSGEEQRYTCHVQH
EGLPEPLMLRWKQ (SEQ ID NO:5)

Alpha1-Alpha3 (HLA-G6) Peptide alpha1   GSHSMRYFSAAVSRPGRGEPRFIAMGYVDDTQFVRFDSDSACPRME
         PRAPWVEQEGPEYWEEETRNTKAHAQTDRMNLQTLRGYYNQSEADP alpha3   PKTHVTHHPVFDYEATLRCWALGFYPAEIILTWQRDGEDQTQDVELV
         ETRPAGDGTFQKWAAVVVPSGEEQRYTCHVQHEGLPEPLMLRWKQ (SEQ ID NO:4)

SEQUENCE LISTING

```
<160> NUMBER OF SEQ ID NOS: 6

<210> SEQ ID NO 1
<211> LENGTH: 92
<212> TYPE: PRT
<213> ORGANISM: Homo sapiens

<400> SEQUENCE: 1

Asp Pro Pro Lys Thr His Val Thr His His Pro Val Phe Asp Tyr Glu
1               5                   10                  15
```

Ala Thr Leu Arg Cys Trp Ala Leu Gly Phe Tyr Pro Ala Glu Ile Ile
        20                  25                  30

Leu Thr Trp Gln Arg Asp Gly Glu Asp Gln Thr Gln Asp Val Glu Leu
        35                  40                  45

Val Glu Thr Arg Pro Ala Gly Asp Gly Thr Phe Gln Lys Trp Ala Ala
65              50                  55                  60

Val Val Val Pro Ser Gly Glu Glu Gln Arg Tyr Thr Cys His Val Gln
65              70                  75                  80

His Glu Gly Leu Pro Glu Pro Leu Met Leu Arg Trp
                85                  90

<210> SEQ ID NO 2
<211> LENGTH: 90
<212> TYPE: PRT
<213> ORGANISM: Homo sapiens

<400> SEQUENCE: 2

Gly Ser His Ser Met Arg Tyr Phe Ser Ala Val Ser Arg Pro Gly
1               5                   10                  15

Arg Gly Glu Pro Arg Phe Ile Ala Met Gly Tyr Val Asp Asp Thr Gln
        20                  25                  30

Phe Val Arg Phe Asp Ser Asp Ser Ala Cys Pro Arg Met Glu Pro Arg
        35                  40                  45

Ala Pro Trp Val Glu Gln Glu Gly Pro Glu Tyr Trp Glu Glu Glu Thr
        50                  55                  60

Arg Asn Thr Lys Ala His Ala Gln Thr Asp Arg Met Asn Leu Gln Thr
65              70                  75                  80

Leu Arg Gly Tyr Tyr Asn Gln Ser Glu Ala
                85                  90

<210> SEQ ID NO 3
<211> LENGTH: 108
<212> TYPE: PRT
<213> ORGANISM: Artificial Sequence
<220> FEATURE:
<223> OTHER INFORMATION: Synthetic alpha3-L1 peptide

<400> SEQUENCE: 3

Gly Cys Gly Gly Gly Ser Gly Gly Gly Ser Arg Ala Asp Pro
1               5                   10                  15

Pro Lys Thr His Val Thr His His Pro Val Phe Asp Tyr Glu Ala Thr
        20                  25                  30

Leu Arg Cys Trp Ala Leu Gly Phe Tyr Pro Ala Glu Ile Ile Leu Thr
        35                  40                  45

Trp Gln Arg Asp Gly Glu Asp Gln Thr Gln Asp Val Glu Leu Val Glu
        50                  55                  60

Thr Arg Pro Ala Gly Asp Gly Thr Phe Gln Lys Trp Ala Ala Val Val
65              70                  75                  80

Val Pro Ser Gly Glu Glu Gln Arg Tyr Thr Cys His Val Gln His Glu
                85                  90                  95

Gly Leu Pro Glu Pro Leu Met Leu Arg Trp Lys Gln
                100                 105

<210> SEQ ID NO 4
<211> LENGTH: 184
<212> TYPE: PRT
<213> ORGANISM: Artificial Sequence
<220> FEATURE:
<223> OTHER INFORMATION: Synthetic HLA-G alpha1-alpha3 peptide

<400> SEQUENCE: 4

```
Gly Ser His Ser Met Arg Tyr Phe Ser Ala Val Ser Arg Pro Gly
1               5                   10                  15

Arg Gly Glu Pro Arg Phe Ile Ala Met Gly Tyr Val Asp Asp Thr Gln
            20                  25                  30

Phe Val Arg Phe Asp Ser Asp Ser Ala Cys Pro Arg Met Glu Pro Arg
            35                  40                  45

Ala Pro Trp Val Glu Gln Glu Gly Pro Glu Tyr Trp Glu Glu Glu Thr
50                  55                  60

Arg Asn Thr Lys Ala His Ala Gln Thr Asp Arg Met Asn Leu Gln Thr
65                  70                  75                  80

Leu Arg Gly Tyr Tyr Asn Gln Ser Glu Ala Asp Pro Pro Lys Thr His
                85                  90                  95

Val Thr His His Pro Val Phe Asp Tyr Glu Ala Thr Leu Arg Cys Trp
                100                 105                 110

Ala Leu Gly Phe Tyr Pro Ala Glu Ile Ile Leu Thr Trp Gln Arg Asp
                115                 120                 125

Gly Glu Asp Gln Thr Gln Asp Val Glu Leu Val Glu Thr Arg Pro Ala
130                 135                 140

Gly Asp Gly Thr Phe Gln Lys Trp Ala Ala Val Val Val Pro Ser Gly
145                 150                 155                 160

Glu Glu Gln Arg Tyr Thr Cys His Val Gln His Glu Gly Leu Pro Glu
                165                 170                 175

Pro Leu Met Leu Arg Trp Lys Gln
                180
```

<210> SEQ ID NO 5
<211> LENGTH: 114
<212> TYPE: PRT
<213> ORGANISM: Artificial Sequence
<220> FEATURE:
<223> OTHER INFORMATION: Synthetic alpha3-L2 peptide

<400> SEQUENCE: 5

```
Cys Ala Ser Asp Ser Asp Phe Arg Val Phe Gln Thr Asp Lys Glu Met
1               5                   10                  15

Leu Gln Arg Ala Asp Pro Pro Lys Thr His Val Thr His His Pro Val
            20                  25                  30

Phe Asp Tyr Glu Ala Thr Leu Arg Cys Trp Ala Leu Gly Phe Tyr Pro
            35                  40                  45

Ala Glu Ile Ile Leu Thr Trp Gln Arg Asp Gly Glu Asp Gln Thr Gln
50                  55                  60

Asp Val Glu Leu Val Glu Thr Arg Pro Ala Gly Asp Gly Thr Phe Gln
65                  70                  75                  80

Lys Trp Ala Ala Val Val Val Pro Ser Gly Glu Glu Gln Arg Tyr Thr
                85                  90                  95

Cys His Val Gln His Glu Gly Leu Pro Glu Pro Leu Met Leu Arg Trp
                100                 105                 110

Lys Gln
```

<210> SEQ ID NO 6
<211> LENGTH: 338
<212> TYPE: PRT
<213> ORGANISM: Homo sapiens

<400> SEQUENCE: 6

```
Met Val Val Met Ala Pro Arg Thr Leu Phe Leu Leu Ser Gly Ala
1               5                   10                  15

Leu Thr Leu Thr Glu Thr Trp Ala Gly Ser His Ser Met Arg Tyr Phe
            20                  25                  30

Ser Ala Ala Val Ser Arg Pro Gly Arg Gly Glu Pro Arg Phe Ile Ala
        35                  40                  45

Met Gly Tyr Val Asp Asp Thr Gln Phe Val Arg Phe Asp Ser Asp Ser
    50                  55                  60

Ala Cys Pro Arg Met Glu Pro Arg Ala Pro Trp Val Glu Gln Glu Gly
65                  70                  75                  80

Pro Glu Tyr Trp Glu Glu Glu Thr Arg Asn Thr Lys Ala His Ala Gln
                85                  90                  95

Thr Asp Arg Met Asn Leu Gln Thr Leu Arg Gly Tyr Tyr Asn Gln Ser
                100                 105                 110

Glu Ala Ser Ser His Thr Leu Gln Trp Met Ile Gly Cys Asp Leu Gly
            115                 120                 125

Ser Asp Gly Arg Leu Leu Arg Gly Tyr Glu Gln Tyr Ala Tyr Asp Gly
    130                 135                 140

Lys Asp Tyr Leu Ala Leu Asn Glu Asp Leu Arg Ser Trp Thr Ala Ala
145                 150                 155                 160

Asp Thr Ala Ala Gln Ile Ser Lys Arg Lys Cys Glu Ala Ala Asn Val
                165                 170                 175

Ala Glu Gln Arg Arg Ala Tyr Leu Glu Gly Thr Cys Val Glu Trp Leu
                180                 185                 190

His Arg Tyr Leu Glu Asn Gly Lys Glu Met Leu Gln Arg Ala Asp Pro
            195                 200                 205

Pro Lys Thr His Val Thr His His Pro Val Phe Asp Tyr Glu Ala Thr
    210                 215                 220

Leu Arg Cys Trp Ala Leu Gly Phe Tyr Pro Ala Glu Ile Ile Leu Thr
225                 230                 235                 240

Trp Gln Arg Asp Gly Glu Asp Gln Thr Gln Asp Val Glu Leu Val Glu
                245                 250                 255

Thr Arg Pro Ala Gly Asp Gly Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Glu Pro Leu Met Leu Arg Trp Lys Gln Ser Ser Leu Pro
    290                 295                 300

Thr Ile Pro Ile Met Gly Ile Val Ala Gly Leu Val Val Leu Ala Ala
305                 310                 315                 320

Val Val Thr Gly Ala Ala Val Ala Ala Val Leu Trp Arg Lys Lys Ser
            325                 330                 335

Ser Asp
```

MULTIMERIC POLYPEPTIDES OF HLA-G INCLUDING ALPHA1-ALPHA3 MONOMERS AND PHARMACEUTICAL USES THEREOF

The present invention relates to multimeric polypeptides and pharmaceutical uses thereof. The invention more specifically relates to multimers comprising alpha1 and alpha3 domains of an HLA-G antigen. The invention also relates to methods of producing such multimers, pharmaceutical compositions comprising the same, as well as their uses for treating various diseases including organ/tissue rejection.

Major histocompatibility complex (MHC) antigens are divided up into three main classes, namely class I antigens, class II antigens (HLA-DP, HLA-DQ and HLA-DR), and class III antigens.

Class I antigens comprise classical antigens, HLA-A, HLA-B and HLA-C, which exhibit 3 globular domains ($\alpha 1$, $\alpha 2$ and $\alpha 3$) associated with beta2 microglobulin, as well as non classical antigens HLA-E, HLA-F, and HLA-G.

HLA-G is a non-classic HLA Class I molecule expressed by extravillous trophoblasts of normal human placenta, thymic epithelial cells and cornea. HLA-G antigens are essentially expressed by the cytotrophoblastic cells of the placenta and function as immunomodulatory agents protecting the foetus from the maternal immune system (absence of rejection by the mother). The sequence of the HLA-G gene has been described [1,2] and comprises 4396 base pairs. This gene is composed of 8 exons, 7 introns and a 3' untranslated end, corresponding respectively to the following domains: exon 1: signal sequence, exon 2: alpha1 extracellular domain, exon 3: alpha1, extracellular domain, exon 4: alpha3 extracellular domain, exon 5: transmembrane region, exon 6: cytoplasmic domain I, exon 7: cytoplasmic domain II (untranslated), exon 8: cytoplasmic domain III (untranslated) and 3' untranslated region.

Seven isoforms of HLA-G have been identified, among which 4 are membrane bound (HLA-G1, HLA-G2, HLA-G3 and HLA-G4) and 3 are soluble (HLA-G5, HLA-G6 and HLA-G7) (see [3] for review).

The mature HLA-G1 protein isoform comprises the three external domains ($\alpha 1$, $\alpha 2$ and $\alpha 3$), the transmembrane region and the cytoplasmic domain.

The HLA-G2 protein isoform does not comprise the $\alpha 2$ domain, i.e., the $\alpha 1$ and $\alpha 3$ domains are directly linked, followed by the transmembrane domain and the cytoplasmic domain.

The HLA-G3 protein isoform lacks both the $\alpha 2$ and $\alpha 3$ domains, i.e., it comprises the $\alpha 1$ domain directly linked to the transmembrane domain and the cytoplasmic domain.

The HLA-G4 protein isoform lacks the $\alpha 3$ domain, i.e., it comprises the $\alpha 1$ domain, the $\alpha 2$ domain, the transmembrane domain and the cytoplasmic domain.

Soluble HLA-G isoforms all lack the transmembrane and cytoplasmic domains. More specifically:

The HLA-G5 protein isoform contains the $\alpha 1$, $\alpha 2$ and $\alpha 3$ domains, as well as an extra C-terminal peptide sequence of 21 amino acid residues encoded by intron 4 (as a result of intron 4 retention after transcript splicing and RNA maturation).

The HLA-G6 protein isoform corresponds to the HLA-G5 without $\alpha 2$, i.e., HLA-G6 contains $\alpha 1$ and $\alpha 3$ domains, as well as an extra C-terminal peptide sequence of 21 amino acid residues encoded by intron 4 (as a result of intron 4 retention after transcript splicing and RNA maturation The HLA-G7 protein isoform contains only the alpha1 domain, as well as 2 additional C-terminal amino acid residues encoded by intron2 (as a result of intron 2 retention after transcript splicing and RNA maturation).

All of these isoforms have been described in [4,5,6] and European Application EP 0 677 582.

Previous studies have shown that HLA-G proteins are able to inhibit allogeneic responses such as proliferative T lymphocyte cell response, cytotoxic T lymphocytes mediated cytolysis, and NK cells mediated cytolysis [7,8,9]. More recent studies have also shown that HLA-G is capable of inducing the differentiation of regulatory T cells, which can then inhibit allogeneic responses themselves, and are known to participate in the tolerance of allografts [10,11]. Because of this broad inhibitory function, it has been shown that the expression of HLA-G correlates with a better acceptance of allogeneic transplants, whether HLA-G is expressed by the graft or is detected in the plasma of patients, as a soluble molecule [12,13,14]. As a result, HLA-G-based procedures have been proposed for treating graft rejection in allogeneic or xenogenic organ/tissue transplantation. HLA-G proteins have also been proposed for the treatment of cancers (EP 1 054 688), inflammatory disorders (EP 1 189 627) and, more generally, immune related diseases. It has also been proposed to fuse HLA-G proteins to specific ligands in order to target HLA-G to particular cells or tissues (WO 2007/091078). It should be noted, however, that no results or experimental data have been provided to show that such targeting fusions are active.

HLA-G has been shown to bind three main receptors: ILT2/LILRB1/CD85j, ILT4/LILRB2/CD85d and KIR2DL4. ILT2 is mainly expressed by T cells, B cells, NK cells, monocytes, and dendritic cells. ILT4 is expressed only by myeloid cells, i.e. mainly monocytes and dendritic cells. KIR2DL4 is mainly expressed by decidual NK cells and by a small subset of peripheral NK cells. Due to the broad expression patterns of its inhibitory receptors, HLA-G may exert its tolerogenic function on all the effectors of immune responses that are responsible for anti-viral immunity, auto-immune reactions, anti-tumor immunity, inflammatory diseases, and rejection of transplants.

KIR2DL4 is a specific receptor for HLA-G. KIR2DL4 docks on the alpha1 domain of HLA-G, and more specifically on residues $Met^{76}$ and $Gln^{79}$ which are characteristic to HLA-G [15]. It was further shown that these two residues are crucial to the inhibitory function of HLA-G through KIR2DL4, and that mutating them prevented the inhibition of cytolytic activity of KIR2DL4-expressing NK cells by HLA-G in vitro. In spite of its specificity for HLA-G, KIR2DL4 is not likely to play a significant role in HLA-G inhibitory function except in the context of pregnancy, mainly because of its expression that is restricted to decidual NK cells, and because in vitro and in vivo, it was shown that ILTs played the key role through interaction with HLA-G alpha3 domain. It is possible that the alpha1 domain of HLA-G plays a direct role in the function of HLA-G, through KIR2DL4 or another, as yet unknown receptor, but the evidence available to date points to a tolerogenic function of HLA-G that is mediated mainly if not entirely by the interaction of its alpha3 domain with ILT2 and ILT4 molecules.

ILT2 and ILT4 are not specific receptors for HLA-G, and it was shown they can bind other HLA Class I molecules through their alpha3 domain [16,17,18]. The capability of the HLA-Class I domain to bind to ILT molecules is well described. ILT2, in particular, has been reported to bind "most if not all" HLA Class I molecules.

However, HLA-G is the ligand of highest affinity for ILT2 and ILT4, as illustrated in Table 1 of Shiroishi et al [19].

Thus ILT2 and ILT4 bind more strongly to HLA-G than to classical HLA class I molecules. (see [20,21]).

This stronger ILT-binding capacity of HLA-G compared to other HLA Class I molecules is particularly well illustrated by the fact that HLA-G at the surface of tumor cells, but not classical HLA class I molecules are capable to engage the ILT2 and/or ILT4 receptors of cytolytic effectors with sufficient strength to block the function of these effectors and thus protect the tumor cells from immune destruction [22].

ILT2 and ILT4 do not bind the same HLA-G structures [21]. Indeed, ILT2 recognizes only β2 microglobulin (β2m)-associated HLA-G structures, whereas ILT4 has the capability to recognize both β2m-associated and (β2m-free HLA-G heavy chains [21,23]. Yet, ILT4 clearly binds β2m-free HLA-G heavy chains better that β2m-associated ones.

HLA-G antigen appears to adopt a dimer conformation in vivo as a result of the formation of an intermolecular disulfide bridge between cysteine residue 42 of the α1 domains of two HLA-G molecules [20,23 and 25; WO2007/011044].

The dimeric structure of HLA-G has been described in Shiroishi et al. [20]. Two molecules of wild-type HLA-G exist in an asymmetric unit; each monomer is covalently attached with the symmetrical partner via the Cys42-Cys42 disulfide bridge along with 2-fold crystallographic axis. The full-length HLA-G1 protein is composed of H chain, associated β2-microglobulin (β2m) and a nonameric peptide similar to the classical MHC class I structure. It has been proposed that receptor binding sites of HLA-G dimers are more accessible than those of corresponding monomers, so that dimers would have a higher affinity and slower dissociation rate than monomers. However, it is not clear what conformation is the most active for pharmaceutical purpose, which isoform is the most efficient, or how appropriate HLA-G dimers or oligomers may be produced.

It emerges from the foregoing that the superior inhibitory function of HLA-G is due:

1. To a unique sequence of its alpha 3 domain which confers it a better ILT-binding capacity than that of other HLA Class I molecules. This unique sequence of the HLA-G alpha 3 domain, as it emerges from FIG. 3 of Shiroishi et al., [21] leads to the creation of larger, more hydrophobic, and stronger ILT-binding area.

Figure 4:
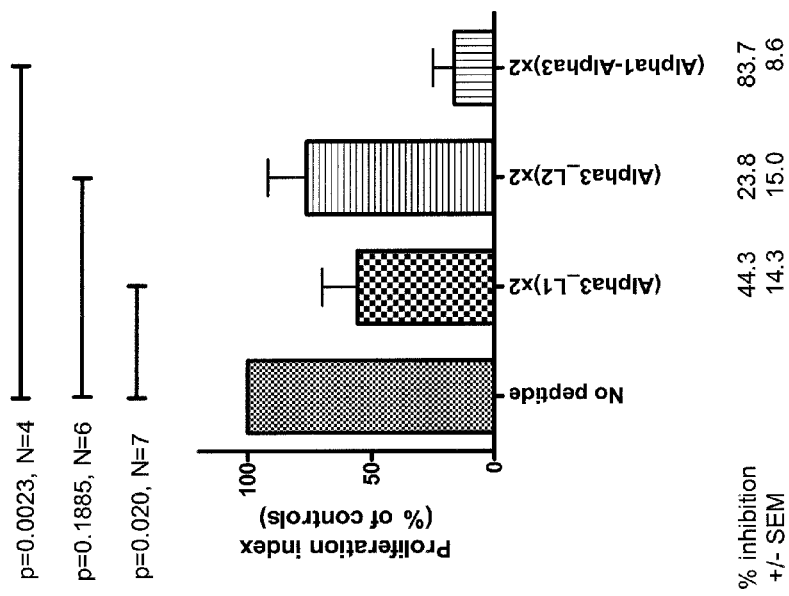

2. To its unique ability to dimerize. Dimerization of HLA-G occurs via the creation of disulfide bridges between the cysteins in position 42 (alpha 1 domain) of two HLA-G molecules (see FIG. 8 of Gonen-Gross et al. [24]) and is crucial to HLA-G function. Indeed, it was shown that mutant HLA-G molecules that lack the cysteine in position 42 and do not make dimers also lack inhibitory function [24]. FIG. 4 of Shiroishi et al [20] provides the disulfide linked HLA-G dimer structure.

Thus, to summarize the data on HLA-G inhibitory function: it goes mainly through the binding of HLA-G dimers to ILT molecules through their unique alpha3 domain. However, the ILT4/HLA-G complex structure [21] reveals that ILT4 shows remarkably distinct major histocompatibility class I (MHCI) binding recognition compared to ILT2, binding more to the β3 domain than to β2m.

Producing HLA-G through cell lines may be tedious. Indeed, the complete HLA-G1/G5 molecule is a trimolecular complex of a HLA-G complete heavy chain (α1, α2 and α3 domains) non-covalently associated with β2m and a nonapeptide. The function of such a construct is well established, but due to the complexity of its structure, its production is difficult, its purification risky, and its stability is poor.

The Inventors have now found that unexpectedly, multimers of small peptides containing alpha1 and alpha3 domains, which may be obtained synthetically, are functional, more pure, therefore more stable, easier to produce because they do not require neither extraction from biological fluids nor specific control (because production does not involve biological agents), thus decreasing the risk of biohazard, following GMP practices: because GMP practices have safety standards in terms of biohazard which are lifted here.

Thus, the present invention relates to multimers or multimeric polypeptides, characterized in that they comprise at least two monomers, each of said monomers being selected in the group consisting of a peptide P2 (named also here after alpha1-alpha3 monomer) of formula P1-X3 or X2-X3, wherein P1 is of formula X1-X2, wherein X1 represents a peptidic linker including a cysteine amino acid and X2 represents an alpha1 domain (or alpha1 peptide) of HLA-G and X3 represents an alpha3 domain (or alpha3 peptide) of HLA-G.

Thus the multimers of the invention include:
Dimers and multimers comprising monomers consisting of a peptidic linker(X1)+alpha1(X2)+alpha3(X3) and/or monomers consisting of alpha1(X2)+alpha3 (X3); and
Dimers and multimers (P2)n, comprising exclusively alpha1+alpha3 monomers X2-X3, as defined above (with n being an integer≥2); among said multimers, are included:
homomultimers of alpha1-alpha3 monomers (n P2 monomers), wherein all the monomers are identical; and
heteromultimer of alpha1-alpha3 monomers (n P2 monomers), wherein the alpha3 and/or alpha1 domains are different in different monomers).

The multimers according to the invention thus include dimers, as well as molecules comprising 3, 4, 5, 6, 7 or even more monomers as defined here above. Multimers according to the instant invention may comprise up to 100, 500, 1000 or even more of said monomers.

The alpha1-alpha3 monomers of the instant invention may also be named alpha3-alpha1 monomers, even though the alpha1 domain is always at the N-terminal end of said monomers.

The inventors have found, unexpectedly, that alpha1-alpha3 multimers are significantly active on all liquid tumors compared to both alpha3-alpha3 multimers and soluble forms of HLA-G (HLA-G5 and HLA-G6).

Liquid tumors are tumors wherein malignant cells circulate in a liquid (blood or lymphatic system) and wherein there is an anormal proliferation of said malignant cells.

Liquid tumors include tumors of lymphoid and myeloid origin; more precisely they include both blood tumors (leukaemia) and blood-forming organ tumors [mainly bone narrow tumors (myeloma, macroglobulinemia) and lymph node tumors (lymphoma)].

Indeed alpha1-alpha3 multimers are unexpectedly active both on lymphoid cell tumors and myeloid cells tumors.

Thus they are specifically active against liquid tumors expressing ILT2 and/or ILT4, such as, for example leukaemias of lymphocytic origin (ex: B Cell Lymphocytic Leukaemia, or T cell lymphocytic leukaemia), or leukaemias of myelocytic origin (ex acute and/or chronic myelomonocytic leukaemia). More specifically, the inventors have surprisingly found that alpha1-alpha3 peptides, when correctly assembled in multimers, have the ability to inhibit growth of liquid tumors.

The results obtained show that the multimers according to the instant invention are effectively active against both lymphoid tumors and myeloid tumors.

It is surprising that multimers of alpha1-alpha3 monomers be effectively active against both tumors of lymphoid cells (ILT2+/ILT4−) and myeloid cells (ILT2+/ILT4+).

Indeed, this is contrary to what is usually known, as regards the role of HLA-G in solid tumors to escape the immune system.

These multimers thus represent very valuable drug candidates for treating such liquid tumors. Control dimers comprise two monomers, each monomer corresponding to peptides comprising a peptidic linker L1 or L2 as defined in FIGS. 8 and 9 and in the examples, i.e. including a cysteine amino acid and an alpha3 domain (or alpha3 peptide) of HLA-G [(alpha3-L1 of SEQ ID NO:3)x2 and (alpha3-L2 of SEQ ID NO:5)x2)].

According to the instant invention:

peptide P1 may also at the C-terminal end and/or at the N-terminal end of X2 comprise less than 20, more preferably less that 15 and most preferably less than 10 or 5 additional amino acids which flank the alpha1 domain in a native HLA-G isoform.

The peptidic linker X1 comprises at least 10-30 amino acids and includes a cysteine at its N-terminal end, preferably in positions 1, 2, 3 or 4 from the N-terminal end; it may be longer to gain more flexibility (up to 100 amino acids).

X2 comprising an alpha1 domain or peptide designates a peptide comprising the amino acid sequence of an alpha1 domain of an HLA-G antigen, or a functional fragment thereof, and essentially devoid of other HLA-G domains. More preferably, the alpha1 peptide comprises the amino acid sequence of an alpha1 domain of a HLA-G antigen. In a multimer of the invention, it is preferred that all alpha1 peptides (or domains) have the same amino acid sequence. However, it is also contemplated that alpha1 peptides of different sequence are present in a multimer of the invention.

X3 comprising an alpha3 domain or peptide designates a peptide comprising the amino acid sequence of an alpha3 domain of an HLA-G antigen, or a functional fragment thereof, and essentially devoid of other HLA-G domains. More preferably, the alpha3 peptide comprises the amino acid sequence of an alpha3 domain of a HLA-G antigen. In a multimer of the invention, it is preferred that all alpha3 have the same amino acid sequence. However, it is also contemplated that alpha3 peptides of different sequence are present in a multimer of the instant invention. More preferably, the alpha3 peptide comprises the amino acid sequence of the a3 domain of an HLA-G antigen.

The alpha3 domain of HLA-G is encoded by exon 4 and corresponds to amino acids 207-298 of the human HLA-G of SEQ ID NO:6.

The alpha1 domain of HLA-G is encoded by exon 2, and corresponds to amino acids 25-114 of the human HLA-G of SEQ ID NO:6.

A "functional fragment" designates a fragment which retains the ability to induce tumor growth inhibition in vivo or in vitro. More preferably, a functional fragment of either alpha3 or alpha1 peptides comprises at least 20, more preferably at least 30, 40 or 50 consecutive amino acids of the alpha3 or alpha1 domain.

In a typical embodiment, the functional fragment contains at least 60 consecutive amino acids of the alpha 1 domain or the alpha3 domain. The functionality of the fragment may be verified as disclosed in the experimental section. In particular, the functionality may be verified by preparing a multimer of the fragments, administering the multimer to an animal model and verifying the tumor inhibition rate. The functionality may also be verified by preparing a multimer of the fragments, adding the multimers to tumor cell culture medium, and verifying the tumor inhibition rate. Where the multimer inhibits the tumor growth by at least 50%, as compared to placebo, the fragment may be considered as functional.

The amino acid sequence of the α1 and α3 domains can be derived directly from the publications of Geraghty et al. [1], or Ellis et al. [2]. These sequences are also available on line (see for instance Genebank numbers for HLA-G: first cloning of genomic sequence: Geraghty et al, PNAS 1987: PubMed ID: 3480534, GeneID: 3135; First cloning of HLA-G1 cDNA: Ellis et al Journal of Immunology 1990. PubMed. ID : 2295808).

Furthermore, the sequences of HLA-G5, HLA-G6 and HLA-G7 are also available from U.S. Pat. No. 5,856,442, U.S. Pat. No. 6,291,659, FR2,810,047, or Paul et al., Hum. Immunol 2000; 61: 1138, from which the sequence of the alpha1 and alpha3 domains can be obtained directly.

It should be understood that natural variants of HLA-G antigens exist, e.g., as a result of polymorphism, which are included in the present application. Also, variants of the above sequences which contain certain (e.g., between 1 and 10, preferably from 1 to 5, most preferably 1, 2, 3, 4 or 5) amino acid substitutions or insertions are also included in the present invention.

the term "multimer" (or multimeric polypeptide) designates a molecule (or a composition or product) comprising at least two monomers as defined above i.e. alpha1-alpha3 (or alpha3-alpha1) monomers associated together through a disulfide bridge or a carrier.

In a specific embodiment, the alpha3 peptide consists essentially of amino acids 183-274 of a mature HLA-G antigen, or a functional fragment thereof.

In a specific embodiment, the alpha 1 peptide consists essentially of amino acids 1-90 of a mature HLA-G antigen, or a functional fragment thereof.

The sequence of a preferred alpha3 peptide is provided in SEQ ID NO:1.

The sequence of a preferred alpha1 peptide is provided in SEQ ID NO:2.

The sequence of an alpha3 monomer is provided in SEQ ID NO:3. The linker corresponds to positions 1-12 and contains a cysteine in position 2; positions 13 and 14 correspond to two amino acids of the alpha2 domain (see SEQ ID NO:6 corresponding to HLA-G and in which alpha2 corresponds to positions 115-206). Positions 15-106 correspond to the alpha3 domain and positions 107-108 correspond to two amino acids of the transmembrane domain; all the hydrophilic tail of HLA G may be inserted. Main contact residues with ILT molecules are in positions 27 and 29.

Another sequence of an alpha3 monomer is provided in SEQ ID NO:5. The linker corresponds to positions 1-18 and contains a cysteine in position 1; positions 19 and 20 correspond to two amino acids of the alpha2 domain (see SEQ ID NO:6 corresponding to HLA-G and in which alpha2 corresponds to positions 115-206). Positions 21-111 correspond to the alpha3 domain and positions 112-113 correspond to two amino acids of the transmembrane domain.

The sequence of a preferred alpha1-alpha3 monomer is provided in SEQ ID NO:4. Positions 1-90 of SEQ ID NO:4 correspond to alpha1 domain; positions 91-182 of SEQ ID NO:4 correspond to alpha3 domain and positions 183-184 correspond to two amino acids of the transmembrane domain; all the hydrophilic tail of HLA G may be inserted. Cys42 is used for dimerization. Main contact residues with ILT molecules are in positions 103 and 105.

Within multimers of the instant invention, the various monomers may be linked together in different manner such as, without limitation, through disulfide bridging (especially for a dimer), or through a spacer group and/or a carrier.

In a preferred embodiment of the instant invention, the alpha3-alpha1 monomers as defined here above are linked covalently or through an affinity interaction.

A particular example of a multimer of the invention is a dimer.

In this respect, the invention relates to an alpha1-alpha3 dimer, having two monomers of SEQ ID NO:4, wherein the two alpha1 peptides are linked through a disulfide bridge. More specifically, the two alpha1 peptides are linked through a disulfide bridge between cysteine residues at amino acid position 42 in human HLA-G antigens.

In a further particular embodiment, the alpha3-alpha1 monomers are linked through a spacer or a carrier. In a particular embodiment, monomers are linked to a carrier, thereby producing a multimer. The carrier can be of different nature. It is preferably biocompatible, and most preferably biologically inert. The carrier may be a molecule, such as a protein, e.g., albumin (e.g., human serum albumin), or an inert solid carrier. The monomers may be linked to the carrier through different types of coupling reactions, such as affinity interaction or the use of functional groups. Affinity interaction may be obtained by coating the carrier with ligands that bind alpha3 or alpha1 peptides (e.g., antibodies or fragments thereof). Affinity interaction may also be obtained by adding to the alpha3-alpha1 monomers and to the carrier, respectively a member of a binding pair (e.g., avidin and biotin). Coupling may also be obtained through bi-functional groups such as maleimide, etc. Furthermore, it should be noted that multimers may contain monomers linked to a carrier and further engaged in inter-molecular disulfide bridging.

In a particular embodiment, a multimer of the instant invention is a molecule comprising two or more alpha3-alpha1 monomers linked to a carrier.

The multimers of this invention can be produced by various techniques. As discussed above, the monomers may be coupled together through different coupling techniques, such as covalent linkage (e.g., disulfide bridge, bi-functional group, etc) or affinity reaction.

For the production of a multimer through disulfide linkage:

Alpha3 monomers of SEQ ID NO:3 or SEQ ID NO:5 were synthesized chemically. Monomers were first synthesized, Dimerization was then performed by generating a disulfide bridge between the cysteines within the linker X1 of two monomers (Cysteine 2 of SEQ ID NO:3 or cysteine 1 of SEQ ID NO:5). The purity of the synthesized products was verified by mass spectrometry.

alpha3-alpha1 monomers: in a first step alpha1-alpha3 peptides are synthesized chemically; in a second step, alpha1-alpha3 monomers are refolded by allowing the generation of disulfide bonds between the two cysteins within the alpha3 domain (cysteines 111 and 167 of SEQ ID NO:4). In a third step, dimers are obtained by generating a disulfide bridge between the free cysteins of the alpha1 domain of two monomers (Cysteine 42 of SEQ ID NO :4). In a fourth step and, preferably, the dimers or multimers are separated. Multimers may be separated from monomers, e.g., on the basis of their molecular weight, e.g., by gel electrophoresis (such as PAGE). The suitable formation of multimers may also be verified using such method on aliquot samples, to measure the relative amount of multimer present in the solution and, if necessary, adjust the reaction condition. Conditions allowing formation of disulfide linkage include, for instance, a temperature of 10-30° C. for 2-24 hours. Step 2 may alternatively be performed prior to step 1.

alpha3 monomers, wherein the alpha3 peptide comprises a linker comprising a lateral SH group are prepared in the same conditions as specified above for the alpha3-alpha1 multimers (steps 2 and 3).

For the production of a multimer through the use of a carrier, the monomers are typically incubated in the presence of the carrier under conditions allowing attachment of the monomers on the carrier and, preferably, the multimer is separated. The carrier may be e.g., a solid carrier. The carrier may also be a protein, such as serum-albumin. In order to facilitate interaction between the monomers and the carrier, the carrier may be functionalized to contain reactive groups able to interact with the monomers. As an example, the carrier may be coated with a ligand of alpha1 or alpha3 peptides, such as antibodies or fragments thereof (e.g., Fab fragments, CDR fragments, ScFv, etc) or a chemical coupling reagent (e.g., maleimide). Alternatively, the carrier may be functionalized by a reactant able to bind a ligand of the alpha1 polypeptides. As an example, the carrier may be coated with an anti-human IgG Fc fragment, and the ligand may be a human polyclonal IgG directed against an HLA-G1 antigen. In such a case, the monomers, carrier and ligand may be incubated together, in order to allow proper association of the monomers to the beads.

Alpha1-alpha3 multimers of the invention may be produced by techniques known per se in the art, such as recombinant techniques, enzymatic techniques or artificial synthesis, preferably by artificial synthesis, such as Merrifield synthesis.

Alpha3 multimers may be also produced by techniques known per se.

In a preferred embodiment, the alpha3 and alpha1-alpha3 peptides are produced by artificial synthesis using known chemistry and synthesisers.

The alpha1-alpha3 multimers may comprise either natural amino acids, or non-natural or modified amino acid residues. They may be in L and/or D conformation. The peptides may comprise either amine linkages and/or modified peptidomimetic linkages. Also, the peptides may be terminally protected and/or modified, e.g., through chemical or physical alteration of lateral functions, for instance.

In further embodiment, the carrier and monomers may be modified to contain cross-reactive groups (e.g., avidin and biotin). In such a case, incubation of the carrier and monomers will cause multimerisation on the carrier.

The multimer formed (i.e., the complex between the carrier and the alpha3-alpha1 monomer) can be isolated using various techniques known per se in the art, including centrifugation, sedimentation, electromagnetic separation, etc.

Specific examples of multimers of the invention are:
multimers of alpha3-alpha1 monomers of SEQ ID NO:4 linked through disulfide bridge; and
multimers of alpha3-alpha1 monomers of SEQ ID NO:4 linked to a carrier.

As mentioned in the examples, these multimers are able to promote liquid tumor inhibition (tumors of lymphocytic origin and tumors of myeloid origin).

Furthermore, the dimers of alpha3-alpha1 monomer of SEQ ID NO: 4 also represent specific objects of the invention. The invention indeed shows that said dimers have substantial in vivo activity for treating liquid tumors and may be used to prepare very active multimers.

The invention also relates to a pharmaceutical composition comprising a multimer as defined above or obtainable by a method as disclosed above and, preferably, at least a pharmaceutically acceptable vehicle or carrier.

A further object of this invention is a pharmaceutical composition comprising an alpha3-alpha1 dimer having two monomers of SEQ ID NO:4 and, preferably, at least a pharmaceutically acceptable vehicle or carrier.

Suitable vehicles or carriers include any pharmaceutically acceptable vehicle such as buffering agents, stabilizing agents, diluents, salts, preservatives, emulsifying agents, sweeteners, etc. The vehicle typically comprises an isotonic aqueous or non aqueous solution, which may be prepared according to known techniques. Suitable solutions include buffered solutes, such as phosphate buffered solution, chloride solutions, Ringer's solution, and the like. The pharmaceutical preparation is typically in the form of an injectable composition, preferably a liquid injectable composition, although other forms may be contemplated as well, such as tablets, capsules, syrups, etc. The compositions according to the invention may be administered by a number of different routes, such as by systemic, parenteral, oral, rectal, nasal or vaginal route. They are preferably administered by injection, such as intravenous, intraarterial, intramuscular, intraperitoneal, or subcutaneous injection. Transdermal administration is also contemplated. The specific dosage can be adjusted by the skilled artisan, depending on the pathological condition, the subject, the duration of treatment, the presence of other active ingredients, etc. Typically, the compositions comprise unit doses of between 10 ng and 100 mg of multimer, more preferably between 1 µg and 50 mg, even more preferably between 100 µg and 50 mg. The compositions of the present invention are preferably administered in effective amounts, i.e., in amounts which are, over time, sufficient to at least reduce or prevent disease progression. In this regard, the compositions of this invention are preferably used in amounts which allow the reduction of a deleterious or unwanted immune response in a subject.

Said multimeric polypeptides can be used as tolerogenic agents capable of mimicking HLA-G full function. The prime therapeutic uses of these compounds would be transplantation, in order to induce and maintain tolerance to allografts, but may also be auto-immune diseases, or inflammatory diseases, in order to stop auto-immune responses and inflammation, and possibly re-establish auto-tolerance. The advantages of such polypeptides are production/purification protocols comparatively easier, cheaper, more controlled, and safer than classical production methods that involve prokaryotic or eukaryotic organisms.

As mentioned above, the multimers of the instant invention have strong anti-tumoral activity against liquid tumors and therefore may be used to treat liquid tumors.

The instant invention also relates to a multimer or a pharmaceutical composition as disclosed here above for treating liquid tumors (leukaemia and myeloid tumors).

It should be understood that the amount of the composition actually administered shall be determined and adapted by a physician, in the light of the relevant circumstances including the condition or conditions to be treated, the exact composition administered, the age, weight, and response of the individual patient, the severity of the patient's symptoms, and the chosen route of administration. Therefore, the above dosage ranges are intended to provide general guidance and support for the teachings herein, but are not intended to limit the scope of the invention.

Besides the above provisions, the invention also comprises other provisions that will emerge from the following description, which refers to examples of implementation of the present invention and also to the attached drawings, in which:

FIG. 1: 3D model of the (alpha3)x2 polypeptide. A Model of the dimerized polypeptide. Each monomer is in a different grey. The artificially introduced free cysteine is shown by spheres, allowing dimerization. B: Superimposition of the structure of the alpha3 peptide with that of the complete HLA-G molecule. HLA-G complete molecule (including beta-2 microglobulin and peptide) is shown in light threads. Alpha3 peptide is shown in 3D ribbon rendering. The structures of the alpha3 domain of HLA-G and of the alpha3 peptide are superimposed.

Figure 2:
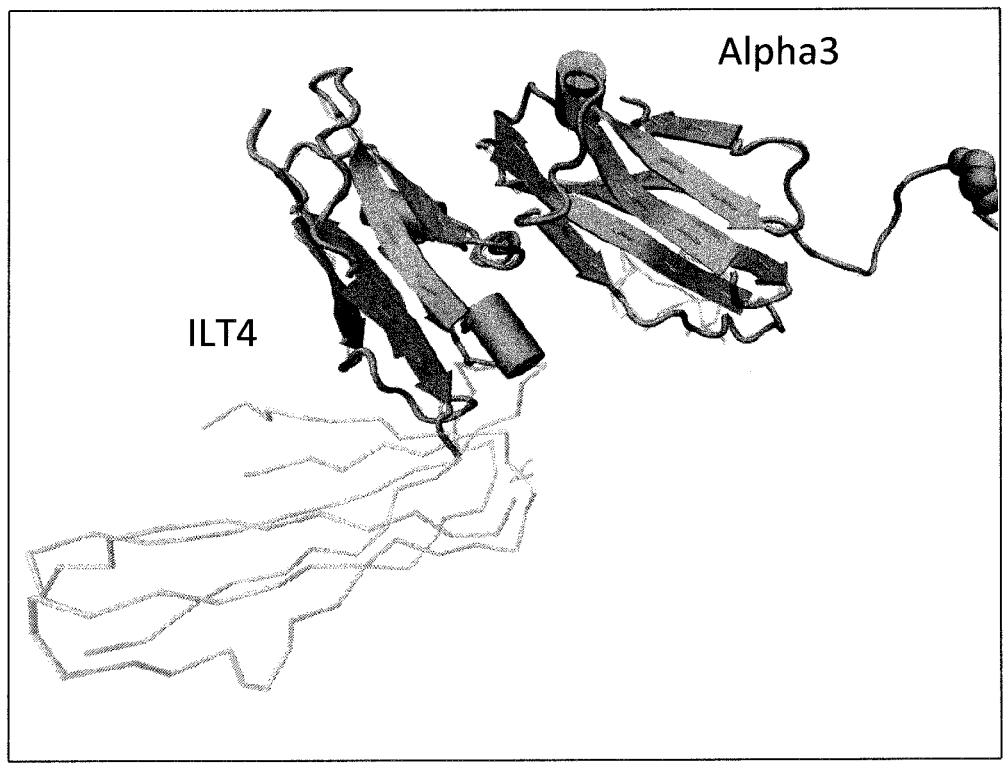

FIG. 2: 3D model of the binding of the (Alpha3)x2 polypeptide to ILT4 molecules. Only one half of the (alpha3) x2 dimer is shown.

Figure 3:
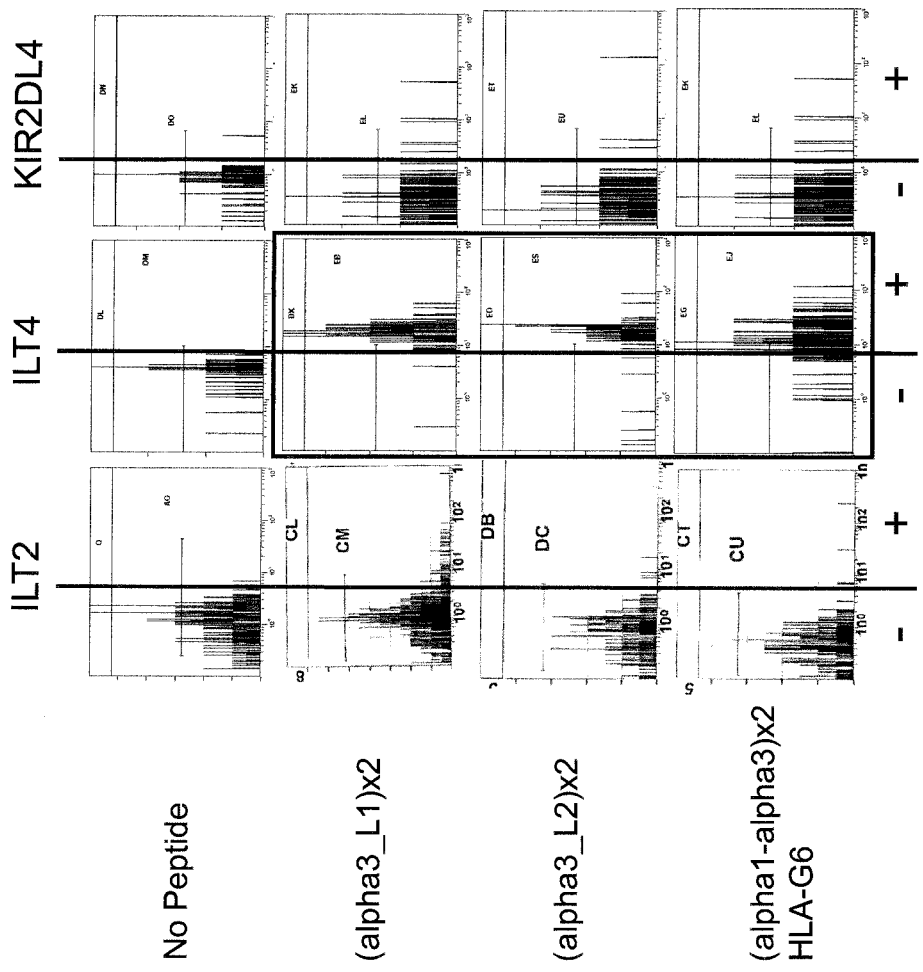

FIG. 3: Binding of different dimers to HLA-G receptors ILT2, ILT4, KIR2DL4: (alpha3-L1)x2: control peptide; (alpha3-L2)x2: control peptide; (alpha3-alpha1)x2: P2-P2 dimer according to the invention.

FIG. 4: Effect of different dimers on the cellular multiplication of the tumor line RAJI (Burkitt's lymphoma) (accession number ATCC CCL-86).

Figure 5:
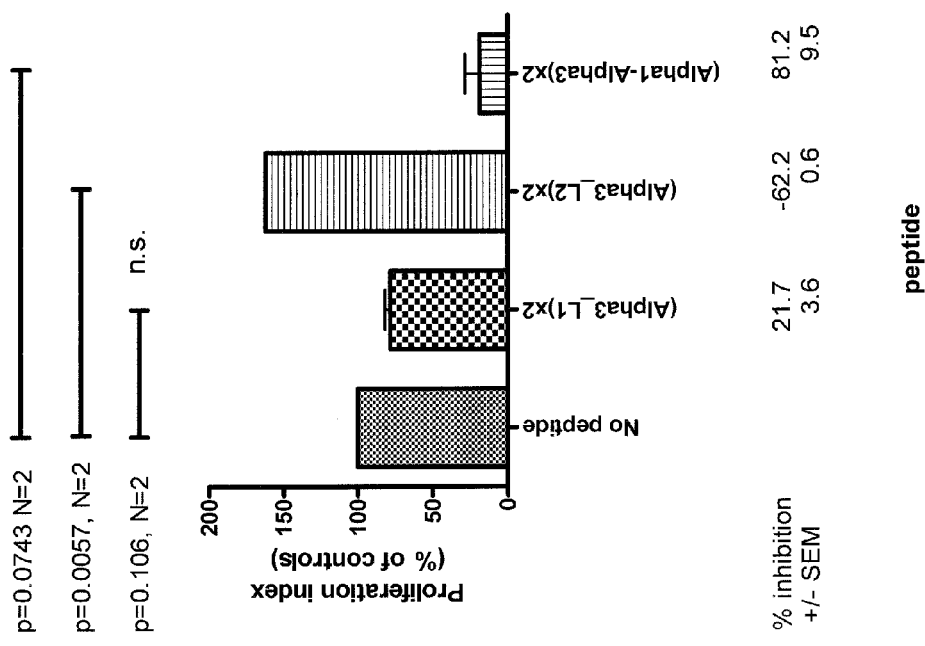

FIG. 5: Effect of different dimers on the cellular multiplication of the tumor line DAUDI (Burkitt's lymphoma) (accession number ATCC CCL-213).

Figure 6:
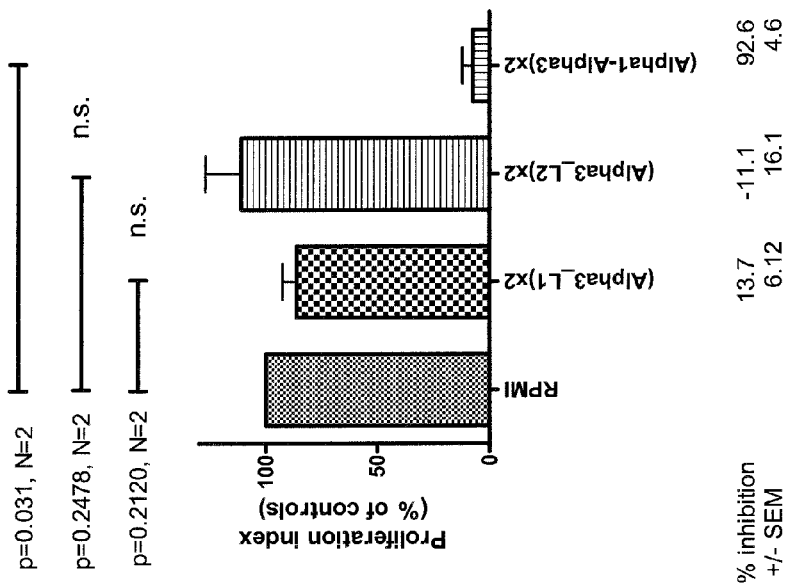

FIG. 6: Effect of different dimers on the cellular multiplication of the tumore line U937 (Histiocytic lymphoma-monocyte) (accession number CLR-1593.2).

Figure 7:
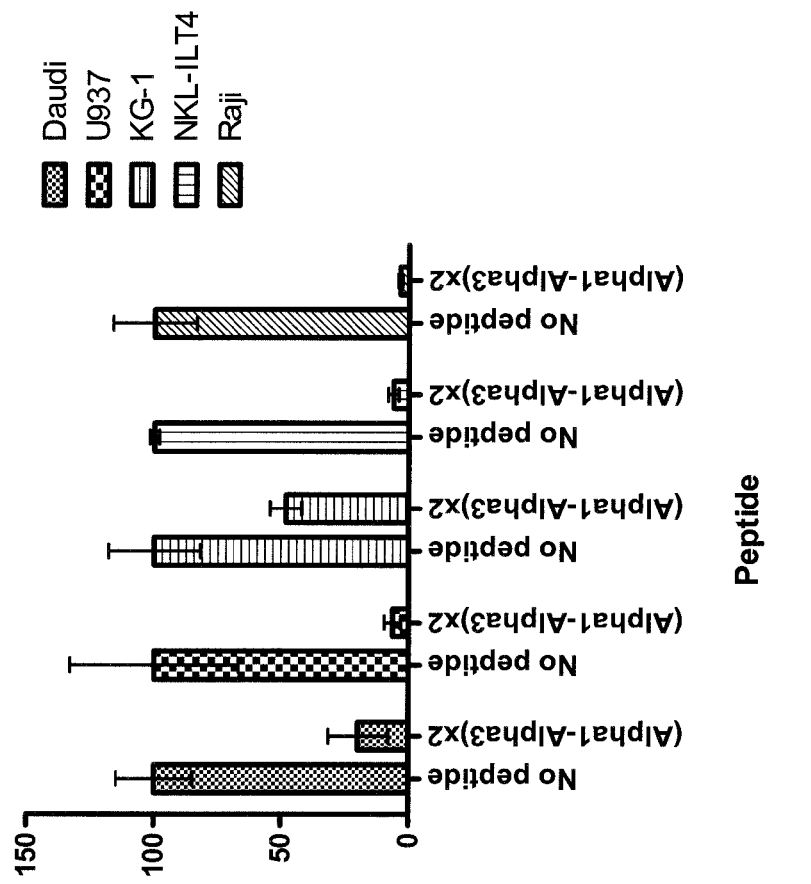

FIG. 7: Sum up of the effects of different dimers on cellular multiplication of different malignant cell lines (Daudi, accession number CCL-213; U937, accession number CRL-1593.2; KG1, accession number CCL-246; ILT4-transfected NKL (NKL-ILT4, Robertson M J et al., *Exp Hematol.* 1996, 24:406-415; Raji, accession number CCL-86).

Figure 8:
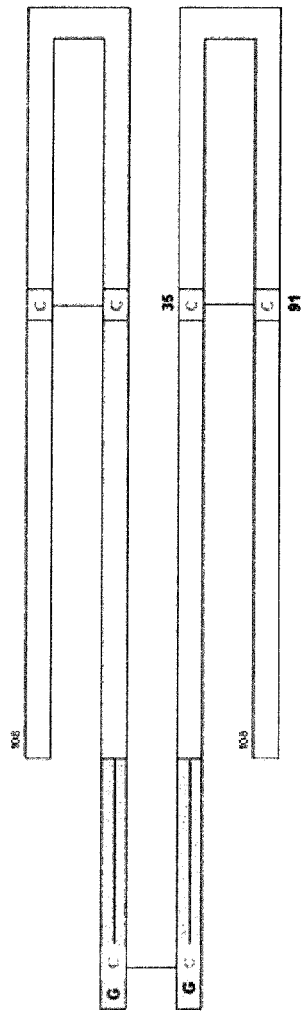

FIG. 8: General structures of control (alpha3-L1)x2 and (alpha3-L2)x2 dimers, including SEQ ID NOs: 3 and 5.

Figure 9:
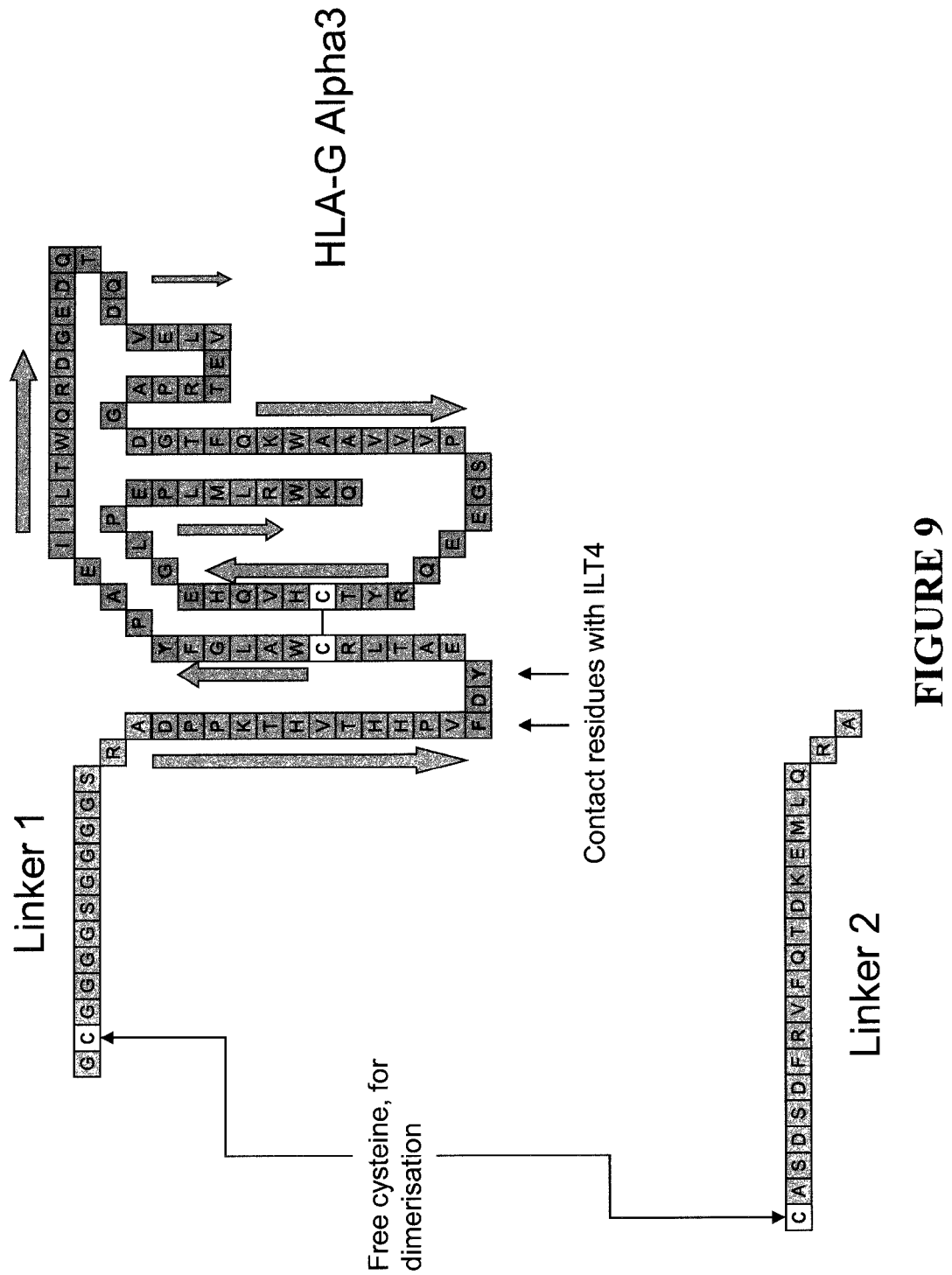

FIG. 9: Structural scheme of control alpha3-L1 and alpha3-L2 monomers, including SEQ ID NO: 3 and residues 1-20 of SEQ ID NO: 5.

Figure 10:
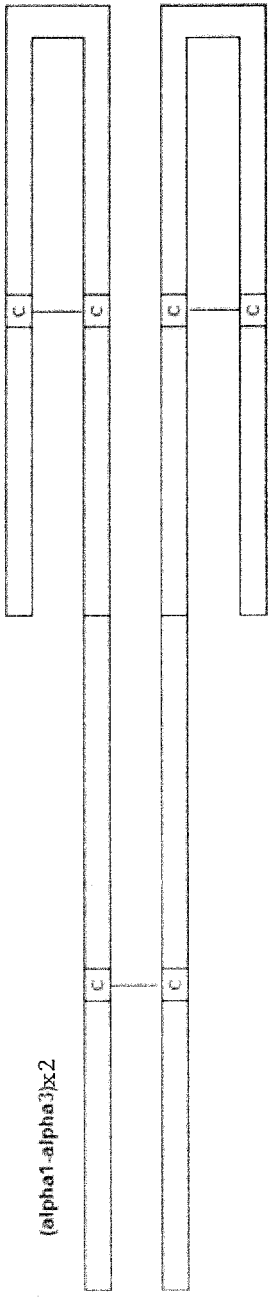

FIG. 10: General structure of (alpha3-alpha1)x2 dimers, including SEQ ID NO: 4.

EXAMPLE 1

Preparation of Peptides of SEQ ID NO:1-5

The peptides of SEQ ID NO:1-5 were synthesised using a peptide synthesiser.

Different dimers have been produced:
- (alpha3-L1)x2 (SEQ ID NO:3), wherein L1 corresponds to a flexible peptidic linker according to the invention, i.e. comprising mainly glycine and serine amino acid residues;
- (alpha3-L2)x2 (SEQ ID NO:5), wherein L2 corresponds to amino acids 1-18 of said SEQ ID NO:5 and is derived from alpha1 amino acid residues 42-30 (from N-terminal and to C-terminal end) of HLA-G (see SEQ ID NO:6);
- (alpha3-alpha1)x2 corresponding to SEQ ID NO:4.

FIGS. 8, 9 and 10 illustrate the general structures of the synthesized peptides.

EXAMPLE 2

Alpha3 and Alpha3-Alpha1 Dimers Through Disulfide Linkage

1) Alpha3 Dimers

Alpha3 monomers of SEQ ID NO:3 or SEQ ID NO:5 were synthesized chemically. Monomers were first synthesized, then refolded by allowing the generation of disulfide bonds between the two cysteines within the alpha3 domain (cysteines 35 and 91 of SEQ ID NO:3, cysteines 41 and 97 of SEQ ID NO:5). Dimerization was then performed by generating a disulfide bridge between the cysteins within the linker X1 of two monomers (Cystein 2 of SEQ ID NO:3, cystein 1 of SEQ ID NO:5). The purity of the synthesized products was verified by mass spectrometry.

Visualization of alpha3 multimers was achieved by eletrophoresis separation: samples were denatured by heat in presence of Laemmli buffer in non-reducing condition (without β-mercaptoethanol), and then separated by electrophoretic migration in a 12% SDS-PAGE. The presence of dimers was then visualized after coloration by coomassie blue.

A three dimensional model of the dimer of SEQ ID NO:3 is shown in FIG. 1. Based on computational modelization, this structure is able to bind HLA-G receptor ILT4 (shown in FIG. 2; see also FIG. 3).

2) Alpha3-Alpha1 Dimers

Alpha3-alpha1 monomers of SEQ ID NO:4 were synthesized chemically. Monomers were first synthesized, then refolded by allowing the generation of disulfide bonds between the two cysteines within the alpha3 domain (cysteines 111 and 167 of SEQ ID NO:4). Dimerization was then performed by generating a disulfide bridge between two cysteins within the alpha1 domain of two monomers (Cysteine 42 of SEQ ID NO:4). The purity of the synthesized products was verified by mass spectrometry.

Visualization of alpha3 multimers was achieved by eletrophoresis separation: samples were denatured by heat in presence of Laemmli buffer in non-reducing condition (without β-mercaptoethanol), and then separated by electrophoretic migration in a 12% SDS-PAGE. The presence of dimers was then visualized after coloration by coomassie blue.

The sequence of the alpha1+alpha3 polypeptide is shown in SEQ ID NO:4.

EXAMPLE 3

Receptor Binding Assays

To test the binding to HLA-G receptors ILT2, ILT4, and KIR2DL4, 12 µg of dimers obtained according to example 2 were covalently coated on Bio-Plex-COOH polystyrene beads (Bio-Rad) according to the manufacturer's recommendations. Beads were then resuspended at a concentration of 2000 beads per 50 µl in 1× Luminex assay buffer (Interchim). Recombinant receptors fused to the Fc part of a human IgG (ILT2-Fc, ILT4-Fc, R&D Biosystems) were then added at 2 µg/ml. Beads and receptors were then incubated for 90 minutes in the dark on a shaker before wash twice with 200 µl of 1×PBS, 0.05% Tween. Beads were then resuspended in 50 µl of PBS Luminex assay Buffer containing 2 µg/ml of Phycoerythrin-conjugated Goat anti Human IgG antibody (Sigma) for 30 minutes in the dark on a rotating shaker. Beads were then washed twice with 200 µl of 1×PBS, 0.05% Tween, and resuspended in 300 µl of 1×PBS.

Fluorescence, indicative of peptide recognition by the receptors was evaluated by flow cytometry performed on an Epics XL Cytometer (Beckman Coulter) using EXPO32 software (Beckman Coulter).

FIG. 3 illustrates the results and clearly show that all peptides containing alpha3 domain indeed bind specifically to ILT4 receptor.

EXAMPLE 4

In vitro Effect of Alpha3-Alpha1 Dimers on Cell Proliferation

The effect of the dimers of example 1 on the multiplication of tumor cell lines was evaluated using the cells lines Raji (B cell, Burkitt's lymphoma; FIG. 4, accession number ATCC CCL-86), Daudi (B cell, Burkitt's Lymphoma; FIG. 5, accession number ATCC CCL-213), U937 (monocytes, histiocytic lymphoma; FIG. 6, accession number CRL-1593.2), KG-1 (myelomonocytic leukaemia; FIG. 7, accession number CCL-246), and ILT4-transfected NKL line (NKL-ILT4, leukaemia, NK cell; FIG. 7, Robertson M J et al., *Exp Hematol.* 1996, 24:406-415) lines. Briefly: 10,000 cells were placed in wells of a 96-well plate in a final volume of 200 µl of culture medium. Peptides were added to obtain a final concentration of 50 µg/ml. All wells were run in duplicates. Cells were incubated for 12 hours prior to addition of tritiated thymidine followed by additional 24 hour incubation at 37° C. and 5% $CO_2$ in a humidified incubator. At the end of the culture, $^3H$ thymidine incorporation into DNA was quantified 18 hours later on a β-counter (Wallac 1450, Amersham Biosciences).

Results presented in FIG. 4 for the tumor line Raji, in FIG. 5 for the tumor line DAUDI, in FIG. 6 for the tumor line U937 show that alpha3-alpha1 dimers (SEQ ID NO:4) inhibit tumor cell multiplication by 83.7%, 81.2%, and 92.6%, respectively. By contrast, alpha3 L2 (SEQ ID NO:5) dimers did not significantly inhibit the proliferation of tumor cell lines, and alpha3 L1 (SEQ ID NO:3) dimers inhibited the proliferation of only one out of three cell lines. FIG. 7 shows specifically the inhibitory effect of alpha1-alpha3 dimers on the proliferation of 5 tumor cell lines of lymphoid and myeloid origin.

Thus, FIGS. 4-7 show that the β3-β1 dimers according to the invention are significantly active against both lymphocyte B tumors and mononuclear cells. This is quite unexpected, considering that B cells are $ILT2^+/ILT4^-$ and mononuclear cells are $ILT2^+/ILT4^+$.

EXAMPLE 5

Production of Alpha3 and Alpha3-Alpha1 Multimers Using a Carrier

Sulfate latex beads (4% w/v 5 µm, Invitrogen) were used as carrier. They were coated with alpha1 monomers either directly or indirectly, i.e., using anti-HLA-G antibody 4H84 capable of recognizing all HLA-G isoforms through their alpha1 domain (0.5 mg/ml, BD Pharmingen).

For indirect coating, $10^8$ Sulfate latex beads were incubated with 20 µg/ml purified anti-human HLA-G Antibody for 2 hrs at 37° C., followed by 2 hr incubation with BSA (2 mg/ml). After washing, the beads were incubated with 1 µg/ml of HLA-G alpha1 peptide (90 mer, produced as in example 1) at 4° C. for 16 hrs.

To generate HLA-G peptide directly coated beads, $10^8$ Sulfate latex beads were coated with 1 µg/ml of HLA-G alpha1 peptide at 4° C. for 16 hrs, followed by 2 hr incubation with BSA (2 mg/ml).

All beads were subsequently washed 2 times by 1×PBS. 5 ml of HLA-G alpha1 peptide (1 µg/ml) was used for $5 \times 10^6$ sulfate latex beads.

Such multimers of the invention were used to induce or increase graft tolerance in vivo.

REFERENCES

1. Geraghty D E, Koller B H, On H T (1987) A human major histo-compatibility complex class I gene that encodes a protein with shortened cytoplasmic segment. Proc Natl Acad Sci USA 84: 9145-9149.
2. Ellis S A, Palmer M S, McMichael. A J (1990) Human trophoblast and the choriocarcinoma cell line BeWo express a truncated HLA Class I molecule. J Immunol 144: 731-735.

3. Carosella, E. D., Dausset, J., Kirszenbaum, M. (1996) HLA-G revisited. Immunol Today 17: 407-409.

4. Kirszenbaum M, Moreau P, Gluckman E, Dausset J, Carosella E (1994) An alternatively spliced form of HLA-G mRNA in human trophoblasts and evidence for the presence of HLA-G transcript in adult lymphocytes. Proc Natl Acad Sci USA 91: 4209-4213.

5. Kirszenbaum M, Moreau P, Teyssier M, Lafon C, Gluckman E, et al. (1995) Evidence for the presence of the alternatively spliced HLA-G mRNA forms in human mononuclear cells from peripheral blood and umbilical cord blood. Hum Immunol 43: 237-241.

6. Moreau P, Carosella E, Teyssier M, Prost S, Gluckman E, et al. (1995) Soluble HLA-G molecule. An alternatively spliced HLA-G mRNA form candidate to encode it in peripheral blood mononuclear cells and human trophoblasts. Hum Immunol 43: 231-236.

7. Rouas-Freiss N, Marchal R E, Kirszenbaum M, Dausset J, Carosella E D (1997) The alpha1 domain of HLA-G1 and HLA-G2 inhibits cytotoxicity induced by natural killer cells: is HLA-G the public ligand for natural killer cell inhibitory receptors? Proc Natl Acad. Sci USA 94: 5249-5254.

8. Rouas-Freiss N, Goncalves R M, Menier C, Dausset J, Carosella E D (1997) Direct evidence to support the role of HLA-G in protecting the fetus from maternal uterine natural killer cytolysis. Proc Natl Acad Sci USA 94: 11520-11525.

9. Rouas-Freiss N, Khalil-Daher I, Riteau B, Menier C, Paul P, et al. (1999) The immunotolerance role of HLA-G. Semin Cancer Biol 9: 3-12.

10. LeMaoult J, Krawice-Radanne I, Dausset J, Carosella E D (2004) HLA-G1-expressing antigen-presenting cells induce immunosuppressive CD4+ T cells. Proc Natl Acad Sci USA 101: 7064-7069.

11. Naji A, Le Rond S, Durrbach A, Krawice-Radanne I, Creput C, et al. (2007) CD3+CD4low and CD3+CD8low are induced by HLA-G: novel human peripheral blood suppressor T-cell subsets involved in transplant acceptance. Blood 110: 3936-3948.

12. Lila N, Carpentier A, Amrein C, Khalil-Daher I, Dausset J, et al. (2000) Implication of HLA-G molecule in heart-graft acceptance. Lancet 355: 2138.

13. Creput C, Durrbach A, Menier C, Guettier C, Samuel D, et al. (2003) Human leukocyte antigen-G (HLA-G) expression in biliary epithelial cells is associated with allograft acceptance in liver-kidney transplantation. J Hepatol 39: 587-594.

14. Qiu J, Terasaki P I, Miller J, Mizutani K, Cai J, et al. (2006) Soluble HLA-G Expression and Renal Graft Acceptance. Am J Transplant 6: 2152-2156.

15. Yan W H, Fan L A (2005) Residues met76 and gln79 in HLA-G alpha1 domain involve in KIR2DL4 recognition. Cell Res 15: 176-182.

16. Colonna M, Navarro F, Bellon T, Llano M, Garcia P, et al. (1997) A common inhibitory receptor for major histocompatibility complex class I molecules on human lymphoid and myelomonocytic cells. J Exp Med 186: 1809-1818.

17. Colonna M, Samaridis J, Cella M, Angman L, Allen R L, et al. (1998) Human myelomonocytic cells express an inhibitory receptor for classical and nonclassical MHC class I molecules. J Immunol 160: 3096-3100.

18. Allan D S, Colonna M, Lanier L L, Churakova T D, Abrams J S, et al. (1999) Tetrameric complexes of human histocompatibility leukocyte antigen (HLA)-G bind to peripheral blood myelomonocytic cells. J Exp Med 189: 1149-1156.

19. Shiroishi M, Tsumoto K, Amano K, Shirakihara Y, Colonna M, et al. (2003) Human inhibitory receptors Ig-like transcript 2 (ILT2) and ILT4 compete with CD8 for MHC class I binding and bind preferentially to HLA-G. Proc Natl Acad Sci USA 100: 8856-8861.

20. Shiroishi M, Kuroki K, Ose T, Rasubala L, Shiratori I, et al. (2006) Efficient Leukocyte Ig-like Receptor Signaling and Crystal Structure of Disulfide-linked HLA-G Dimer. J Biol Chem 281: 10439-10447.

21. Shiroishi M, Kuroki K, Rasubala L, Tsumoto K, Kumagai I, et al. (2006) Structural basis for recognition of the nonclassical MHC molecule HLA-G by the leukocyte Ig-like receptor B2 (LILRB2/LIR2/ILT4/CD85d). PNAS 103: 16412-16417.

22. Caumartin J, Favier B, Daouya M, Guillard C, Moreau P, et al. (2007) Trogocytosis-based generation of suppressive NK cells. EMBO J 26: 1423-1433.

23. Gonen-Gross T, Achdout H, Arnon T I, Gazit R, Stern N, et al. (2005) The CD85J/Leukocyte Inhibitory Receptor-1 Distinguishes between Conformed and {beta}2-Microglobulin-Free HLA-G Molecules. J Immunol 175: 4866-4874.

24. Gonen-Gross T, Achdout H, Gazit R, Hanna J, Mizrahi S, et al. (2003) Complexes of HLA-G protein on the cell surface are important for leukocyte Ig-like receptor-1 function. J Immunol 171: 1343-1351.

25. Boyson J E, Erskine R, Whitman M C, Chiu M, Lau J M, et al. (2002) Disulfide bond-mediated dimerization of HLA-G on the cell surface. Proc Natl Acad Sci USA 99: 16180-16185.

26. Riteau B, Moreau P, Menier C, Khalil-Daher I, Khosrotehrani K, et al. (2001) Characterization of HLA-G1, -G2, -G3, and -G4 isoforms transfected in a human melanoma cell line. Transplant Proc 33: 2360-2364.

27. Lila N, Amrein C, Guillemain R, Chevalier P, Latremouille C, et al. (2002) Human leukocyte antigen-G expression after heart transplantation is associated with a reduced incidence of rejection. Circulation 105: 1949-1954.

The invention claimed is:

1. A multimer, comprising:
   at least two monomers each selected from the group consisting of a peptide P2 consisting of formula P1-X3 and a peptide P2 consisting of formula X2-X3,
   wherein
   P1 is a peptide of formula X1-X2,
   X1 represents a peptidic linker X1 comprising at least 10 and up to 100 amino acids, and the peptidic linker X1 comprising cysteine at or in position 4 or less from the N-terminal end thereof,
   X2 represents an alpha1 domain of HLA-G, and
   X3 represents an alpha3 domain of HLA-G.

2. The multimer of claim 1, wherein
   P1 further comprises less than 20 additional amino acids at the C-terminal end of X2, less than 20 additional amino acids at the N-terminal end of X2, or less than 20 additional amino acids at each of the C-terminal end and the N-terminal end of X2, and
   the additional amino acids flank the alpha1 domain in a native HLA-G isoform.

3. The multimer of claim 1, wherein the monomer of the peptide P2 of formula X2-X3 is provided in SEQ ID NO:4.

4. The multimer of claim 1, wherein the multimer comprises a dimer comprising two monomers of SEQ ID NO:4 associated together through a disulfide bridge between two or more cysteine residues.

5. The multimer of claim 1, wherein the multimer comprises at least two monomers of the peptide P2 of formula X2-X3, and the at least two monomers are linked through a spacer or a carrier.

6. A pharmaceutical composition, comprising:
the multimer of claim 1; and
a pharmaceutically acceptable vehicle or carrier.

7. The multimer of claim 2, wherein P1 comprises less than 15 additional amino acids at the C-terminal end of X2, less than 15 additional amino acids at the N-terminal end of X2, or less than 15 additional amino acids at each of the C-terminal end and the N-terminal end of X2.

8. The multimer of claim 1, wherein the peptidic linker X1 comprises at least 30 and up to 100 amino acids.

9. The multimer of claim 2, wherein the monomer of the peptide P2 of formula X2-X3 is provided in SEQ ID NO:4.

10. The multimer of claim 2, wherein the multimer comprises a dimer comprising two monomers of SEQ ID NO:4 associated together through a disulfide bridge between two or more cysteine residues.

11. The multimer of claim 4, wherein the disulfide bridge is between cysteine residues 42 of the alpha1 domain.

12. The multimer of claim 10, wherein the disulfide bridge is between cysteine residues 42 of the alpha1 domain.

13. The multimer of claim 2, wherein P1 comprises less than 10 additional amino acids at the C-terminal end of X2, less than 10 additional amino acids at the N-terminal end of X2, or less than 10 additional amino acids at each of the C-terminal end and the N-terminal end of X2.

14. The multimer of claim 2, wherein P1 comprises less than 5 additional amino acids at the C-terminal end of X2, less than 5 additional amino acids at the N-terminal end of X2, or less than 5 additional amino acids at each of the C-terminal end and the N-terminal end of X2.

15. The multimer of claim 1, wherein, in the peptide P2 consisting of formula X2-X3, X2 consists of an alpha1 domain of HLA-G, and X3 consists of an alpha3 domain of HLA-G.

16. A method for treating at least one of a lymphoid or a myeloid tumor, the method comprising:
administering the multimer of claim 1 to a mammal in need thereof.

17. A method for treating at least one of a lymphoid or a myeloid tumor, the method comprising:
administering the pharmaceutical composition of claim 6 to a mammal in need thereof.

18. The method of claim 16, wherein the method is suitable for treating a leukaemia tumor, a myeloid tumor, or both.

19. The method of claim 17, wherein the method is suitable for treating a leukaemia tumor, a myeloid tumor, or both.

* * * * *